(12) United States Patent
Von Allmen (10) Patent No.: US 10,162,937 B2
(45) Date of Patent: Dec. 25, 2018

(54) METHOD AND ANALYSIS SYSTEM FOR PROCESSING BIOLOGICAL SAMPLES

(71) Applicant: Roche Diagnostics Operations, Inc., Indianapolis, IN (US)

(72) Inventor: Bernhard Von Allmen, Seengen (CH)

(73) Assignee: ROCHE DIAGNOSTICS OPERATIONS, INC., Indianapolis, IN (US)

( * ) Notice: Subject to any disclaimer, the term of this patent is extended or adjusted under 35 U.S.C. 154(b) by 0 days.

(21) Appl. No.: 14/477,077

(22) Filed: Sep. 4, 2014

(65) Prior Publication Data

US 2015/0066382 A1    Mar. 5, 2015

(30) Foreign Application Priority Data

Sep. 4, 2013 (EP) .................... 13182945

(51) Int. Cl.
| | | |
|---|---|---|
| G01N 33/48 | (2006.01) | |
| G06F 19/00 | (2018.01) | |
| G06F 3/0481 | (2013.01) | |
| G06F 9/451 | (2018.01) | |
| G06G 7/58 | (2006.01) | |
| G01N 35/00 | (2006.01) | |

(52) U.S. Cl.
CPC ............ G06F 19/34 (2013.01); G01N 33/48 (2013.01); G06F 3/0481 (2013.01); G06F 9/453 (2018.02); *G01N 2035/0091* (2013.01)

(58) Field of Classification Search
None
See application file for complete search history.

(56) References Cited

U.S. PATENT DOCUMENTS

| | | |
|---|---|---|
| 6,868,308 B2 | 3/2005 | Ito et al. |
| 8,151,190 B2 | 4/2012 | Taki et al. |
| 9,074,971 B2 | 7/2015 | Ariyoshi |
| 2002/0031444 A1 | 3/2002 | Ito et al. |
| 2005/0114785 A1 | 5/2005 | Finnigan et al. |
| 2006/0053372 A1 | 3/2006 | Adkins et al. |
| 2007/0078631 A1 | 4/2007 | Ariyoshi et al. |
| 2008/0195946 A1 | 8/2008 | Peri-Glass |
| 2010/0205530 A1 | 8/2010 | Butin et al. |

FOREIGN PATENT DOCUMENTS

| | | |
|---|---|---|
| CA | 2 452 993 A1 | 7/2004 |
| CN | 1749960 A | 3/2006 |
| CN | 101091148 A | 12/2007 |
| CN | 102466733 A | 5/2012 |
| EP | 1 637 994 A1 | 3/2006 |
| EP | 2 447 702 A2 | 5/2012 |
| JP | 2006-085683 A | 3/2006 |
| JP | 2006-138779 A | 6/2006 |
| JP | 2007-093297 A | 4/2007 |
| JP | 2008-096182 A | 4/2008 |

OTHER PUBLICATIONS

European Patent Application 13182945.9 Examination Report dated Jan. 3, 2018.
China Patent Application No. 201410448599.5 Office Action dated Jan. 2, 2018. 14 pages.
China Patent Application No. 201410448599.5 Search Report dated Jan. 2, 2018. 3 pages.

*Primary Examiner* — Eric S Dejong
(74) *Attorney, Agent, or Firm* — Woodard, Emhardt, Moriarty, McNett & Henry LLP

(57) ABSTRACT

A method for guiding user input on a computer system of an analysis system that includes an in vitro diagnostic, IVD, device. The IVD device is coupled to the computer system that includes a display, processor, and memory to store applications being executable on the processor. A first application includes instructions that generate on the display a first graphical user interface that includes a set of user interface elements. Each user interface element is positioned in a defined region within the first graphical user interface. The first application includes instructions that control the IVD device to perform an IVD task that includes a sequence of IVD actions. The user activation of the IVD action is performed using a corresponding user interface element. The memory includes geometry data describing a display position for each interface element.

20 Claims, 6 Drawing Sheets

METHOD AND ANALYSIS SYSTEM FOR PROCESSING BIOLOGICAL SAMPLES

CROSS-REFERENCE TO RELATED APPLICATION

This application claims the benefit of European Application No. 13182945.9, filed Sep. 4, 2013, the entire disclosure of which is hereby incorporated by reference.

TECHNICAL FIELD

The disclosure relates to an analysis system for processing biological samples, a method being implemented by the analysis system.

BACKGROUND

The increasing complexity of analytical systems and corresponding laboratory workflows calls for mechanisms which ensure a secure system operation to acquire reliable and accurate data. This is especially true if less trained personnel needs to operate the system in urgent cases (e.g. in the absence of experienced laboratory personnel). Different user support or assistance methods, which provide guidance information to facilitate system operations, are known.

U.S. Pat. No. 6,868,308 B2 discloses an operation guidance method of a clinical system which enables a doctor or nurse unskilled in testing to operate the clinical system without operation error by providing operation guidance.

U.S. Pat. No. 8,151,190 B2 discloses an analysis device allowing any person to utilize job guidance for setting and assignment operations with high efficiency regardless of a level of skill in an automatic analysis device which has a complicated screen configuration with an increase of functions.

SUMMARY

Various embodiments provide a method, and analysis system for processing biological samples as described by the subject matter of the independent claims. Advantageous embodiments are described in the dependent claims.

The term "analysis system" as used herein encompasses any system of lab-devices which are operated and/or monitored collectively. Typically, but not necessarily so, an analysis system comprises one or more analyzers, but the term 'analysis system' may also refer to a system comprising one or more pre-analytical and/or post-analytical devices. For the sake of simplicity, said systems of lab-devices are herein also referred to as 'analysis systems'.

The term "in vitro diagnostic (IVD) task" as used herein encompasses a laboratory procedure to be performed on one or more biological samples. The term further encompasses any processing step to be executed by a user on the lab-device in order to preserve or restore the operability of the lab-device. Accordingly, executing a task may comprise executing an analytical workflow a pre-analytical or post-analytical workflow by a lab-device, e.g. an analyzer or a centrifuge. Executing a task can also comprise evaluating measurement values obtained on one or more samples by a user, e.g. by means of a GUI, or refilling an empty reagent container of a lab-device by said user.

The term "biological sample" refers to any sample that is obtained from or otherwise derived from a biological entity such as an animal.

The term "graphical user interface element" or "user interface element" as used herein may be understood as a user interface object, or a set of user interface objects, displayed on a display screen of a device. A user interface element comprises a button, a text box, a tab, an icon, a text field, a pane, a check-box item, a menu bar, a title bar, an action bar or item group or the like. A user interface element can likewise be an image, a displayed alphanumeric character or any combination thereof.

The term "graphical user interface" or "user interface" as used herein refers to an interface generated by a program for display on a display screen of a device with selectable user interface elements.

In one aspect, the invention relates to an analysis system for processing biological samples. The analysis system comprises an IVD device for performing an analysis of a biological sample.

The IVD device is coupled to a computer system, the computer system comprising a display device; a processor; and memory configured to store a plurality of applications that are executable on the processor. A first application of the plurality of applications comprises instructions that, when executed, generate on the display device a first graphical user interface. The first graphical user interface comprises a set of user interface elements, wherein each user interface element in the set of user interface elements is positioned in a defined region within the first graphical user interface. The first application further comprises instructions that, when executed, control the IVD device to perform an IVD task. The IVD task comprises a sequence of IVD actions; wherein an IVD action is performed in response to user activation of the IVD action, wherein the user activation of the IVD action is performed using a corresponding user interface element of the set of user interface elements. The memory further comprises geometry data describing a display position for each of the set of user interface elements within the first graphical user interface.

A second application comprises instructions that are executed independently of the first application. The two applications are executed independently in the sense that they don't exchange data directly during their executions.

The second application is configured to guide user input to the first graphical user interface for activating the IVD actions of the IVD task, the second application being further configured to: receive task data indicative of the sequence of IVD actions of the IVD task; select from the set of user interface elements a subset of user interface elements that are used to perform the sequence of IVD actions of the IVD task; determine, using the geometry data, a location of each of the subset of user interface elements within the first graphical user interface; determine based on the location of each of the subset of the user interface elements in the first graphical user interface a corresponding display position for displaying information in a second graphical user interface; and display in the corresponding display position of the second graphical user interface, information pertaining to user action to at least one user interface element of the first graphical user interface that activates at least one particular IVD action of the sequence of IVD actions of the IVD task.

According to one embodiment, the user action comprises a user input to the at least one user interface element.

According to another embodiment the user action comprises accepting a notification displayed in the second user interface.

According to one embodiment, upon receiving user inputs to activate the sequence of IVD actions, the IVD device is controlled to perform the IVD task using the received user inputs.

The separation between the guidance application (i.e. second application) and the guided software application (i.e. first application) in a manner that they do not mutually influence or affect each other may avoid that errors, wrong data or other unforeseen issues on the guidance application lead to a changed or possibly wrong behavior of the software application. This is in contrast to the conventional methods in which the guidance is an integrated part of the software application, and thus, any change in the guidance affects the software application. That is, a change in the guidance of the conventional methods requires a validation of the whole software application, while in the present method a change or update on the guidance application does not require a validation of the software application. This may save resources that may be required for the validation process.

In another advantage, these features may provide a flexible guidance that may be automatically adapted to any IVD task that is supported by the software application.

According to one embodiment, the second application is further configured to receive user input to the second graphical user interface that causes the second application to display information pertaining to user action to the first graphical user interface for a previous IVD action or for a subsequent IVD action in the sequence of IVD actions of the IVD task, to cause the second application to display in the second graphical user interface additional or less information regarding user input to the first graphical user interface for the particular IVD action for which information is currently displayed in the second graphical user interface, and/or to call up or switch to a third application that a user can employ to determine an input to the user interface element for the particular IVD action for which information is currently displayed in the second graphical user interface. This embodiment may be advantageous as it may provide a close guidance to the user such that mistakes on data entry or initiation of incorrect actions may be prevented. This may avoid system failures due to wrong inputs and thus may allow a convenient and efficient operation of the analysis system.

According to one embodiment, the second application generates a mask in the second graphical user interface that masks at least part of the first graphical user interface of the display device and prevents access to at least one interface element in the first graphical user interface.

According to one embodiment, the first graphical user interface spatially coincides with the second graphical user interface.

According to one embodiment, the mask generated by the second application in the second graphical user interface prevents access to all interface elements in the first graphical user interface except for at least one interface element in the first graphical user interface that corresponds to the particular IVD action for which the information is currently displayed in the second graphical user interface, thereby allowing a user to interact only with the interface element in the first graphical user interface that relates the particular IVD action to the information being currently displayed in the second graphical user interface.

These embodiments may be advantageous as they may provide a secure mechanism for guidance by preventing erroneous data input to the first application, which may then save resources that would otherwise be required for debugging or reprocessing purpose.

According to one embodiment, the mask generated by the second application in the second graphical user interface is at least partially transparent or semitransparent, thereby permitting a user to continue viewing at least one of the interface elements in the first graphical user interface for which access is prevented. Having an overview on the user elements that are needed to perform the IVD task may further prevent erroneous inputs, as the relations (e.g. visual relation) between the user interface elements may help inputting the right data into the right user interface element.

According to one embodiment, the second application generates an indication (for example, a visual, an audio and/or a tactile indication) and/or displays information in the second graphical user interface when a user attempts to interact with an interface element in the first graphical user interface for which access is prevented by the mask generated by the second application. This may prevent multiple interaction attempts with a user interface element for which access is prevented, and thus may reduce the running time of software applications that may be longer when trying multiple attempts.

According to one embodiment, the first application is further adapted to store the geometry data of the subset of user interface elements in a non-volatile memory space of the memory, wherein the second application is further adapted to monitor the memory content for determining a change in the geometry data, store updated geometry data of the subset of user elements in the non-volatile memory space, and move into a volatile memory of the memory the updated geometry data of the subset of user elements, wherein the determining of the location and the determining of the corresponding display position for displaying information in a second graphical user interface are performed using the updated geometry data.

According to one embodiment, the second application is further adapted to store geometry data of the subset of user elements in a non-volatile memory space of the memory, wherein the second application is further adapted for repeatedly receiving an update status message regarding the geometry data, wherein in case the update status message is indicative of a change in the geometry data, the second application is further adapted to read the memory for determining updated geometry data of the subset of user elements and store the updated geometry data in a non-volatile memory space of the memory, and move in a volatile memory space of the memory said geometry data of the subset of user elements, wherein the determining of the location and the determining of the corresponding display position for displaying information in the second graphical user interface are performed using the updated geometry.

These embodiments may be advantageous as they may save resources required for storing outdated or non-updated geometry data. Storing the non-updated geometry data in the volatile memory may be advantageous as they may still be used e.g. for cross checking purpose, while they are still stored in the volatile memory.

According to one embodiment, the first application is further adapted to store the geometry data of the subset of user interface elements in the memory, wherein the second application is further adapted to monitor the memory content for determining a change in the geometry data or to repeatedly receive an update status message regarding the geometry data, wherein in case the update status message is indicative of a change in the geometry data, the second application is further adapted to read the memory for determining updated geometry data of the subset of user elements, wherein the determining of the location and the determining of the corresponding display position for displaying information in the second graphical user interface are performed using updated geometry data.

According to one embodiment, the memory further comprises an operating system, wherein the operating system comprises a window manager, wherein the window manager is providing the geometry data, wherein the determining of the location and the determining of the corresponding display position for displaying information in the second graphical user interface are performed using the geometry data obtained from the window manager.

According to one embodiment, the generation of the user interface further comprises generating a user interface element in the first graphical user interface that can be selected by a user to start execution of the second application.

According to one embodiment, the generated user interface element comprises a menu bar listing one or more user interface elements, wherein the second application is configured to guide user input to the first graphical user interface for activating the IVD actions of the IVD task upon selecting a user interface element of the one or more user interface elements.

The generated user interface element further comprises a button, a tab, an icon, a pane, a check-box item, an action bar or item group or the like.

According to one embodiment, the second application is executed automatically upon executing at least a part of the first application. This may be advantageous for applications running single IVD tasks, and not requiring user inputs to select a particular IVD task.

According to one embodiment, the computer system comprises a touch screen computer and wherein the display device is a touch sensitive display screen. This is in contrast to tooltips that may not be deployed for touchscreens since there is no pointer. This may be advantageous as the present method may be seamlessly integrated into existing computer systems.

According to one embodiment, the second application is further configured to guide data input to a third graphical user interface for performing a second IVD task, wherein the third graphical user interface is generated by a third application of the plurality of applications stored in the memory. This may be advantageous as it may increase the efficiency of the analysis system since a single guidance application may be used for guiding the user through multiple IVD tasks from multiple applications, such as multiple applications running on one or more analytical systems.

For example, the third application may be started (e.g. from another analyzer) during the guidance of the first application. Alternatively, the third application and the second application may be running in parallel in order to conduct a procedure (which is a combination of the two IVD tasks to be performed by the second and third application) where more than only one analyzer is required.

According to one embodiment, the third graphical interface is displayed in a separate user interface window or on a second display device.

In another aspect, the invention relates to a method for guiding user input to a controller of an analysis system, the analysis system comprising an in vitro diagnostic, IVD, device for performing an analysis of a biological sample, the IVD device being coupled to the controller, the controller comprising a display device; a processor; and memory configured to store a plurality of applications that are executable on the processor, wherein a first application of the plurality of applications comprises instructions that, when executed, generate on the display device a first graphical user interface, the first graphical user interface comprising a set of user interface elements, wherein each user interface element in the set of user interface elements is positioned in a defined region within the first graphical user interface; the first application further comprising instructions that, when executed, control the IVD device to perform an IVD task; wherein the IVD task comprises a sequence of IVD actions; wherein an IVD action is performed in response to user activation of the IVD action, wherein the user activation of the IVD action is performed using a corresponding user interface element of the set of user interface elements; and, wherein the memory further comprises geometry data describing a display position for each of the set of user interface elements; the method comprising:

receiving task data for an IVD task that is indicative of the sequence of IVD actions of the IVD task;

selecting from the set of user interface elements a subset of user interface elements that are used to perform the sequence of IVD actions of the IVD task;

determining, using the geometry data, a location of each of the subset of user interface elements within the first graphical user interface;

determining based on the location of each of the user interface elements of the subset of the user interface elements a corresponding display position for displaying information in a second graphical user interface using the location; and, displaying in the corresponding display position of the second graphical user interface, information pertaining to user action to at least one user interface element of the first graphical user interface that activates at least one particular IVD action of the sequence of IVD actions of the IVD task.

In another aspect, the invention relates to a computer program product comprising computer executable instructions to perform the method steps of the method of the preceding embodiments.

It is understood that one or more of the aforementioned embodiments may be combined as long as the combined embodiments are not mutually exclusive.

BRIEF DESCRIPTION OF THE DRAWINGS

In the following embodiments of the invention are explained in greater detail, by way of example only, making reference to the drawings in which.

DETAILED DESCRIPTION

In the following, like numbered elements in these figures are either similar elements or perform an equivalent function. Elements which have been discussed previously will not necessarily be discussed in later figures if the function is equivalent.

Figure 1:
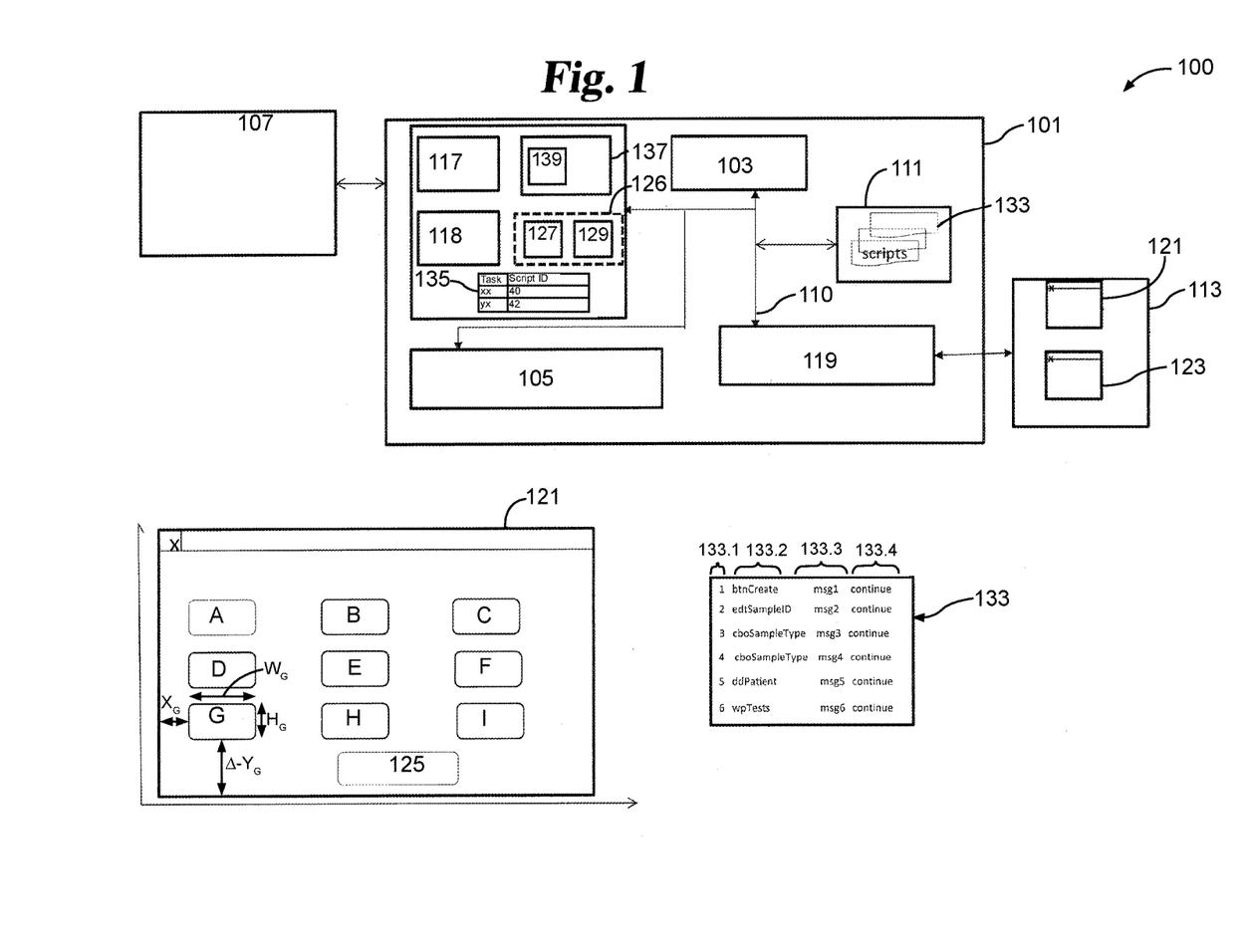
FIG. 1 depicts exemplary analysis system for processing biological samples.

FIG. 1 depicts exemplary analysis system 100 for processing biological samples. The analysis system 100 provides a controller that comprises a computer system 101. The components of computer system 101 may include, but are not limited to, one or more processors or processing units 103, a storage system 111, a memory system 105, and a bus 110 that couples various system components including memory system 105 to processor 103. Memory system 105 may include computer system readable media in the form of volatile memory 117, such as random access memory (RAM) and/or cache memory as well as a non-volatile memory 118.

Computer system 101 may also communicate with one or more external devices such as a keyboard, a pointing device, a display 113, etc.; one or more devices that enable a user to interact with computer system 101; and/or any devices (e.g., network card, modem, etc.) that enable computer system 101 to communicate with one or more other computing devices. Such communication can occur via I/O interface(s) 119. Still yet, computer system 101 can communicate with one or more networks such as a local area network (LAN), a general wide area network (WAN), and/or a public network (e.g., the Internet) via network adapter 109. As depicted, network adapter 109 communicates with the other components of computer system 101 via bus 115. The computer system 101 may be for example a touch screen computer and the display 113 device may be a touch sensitive display screen.

The computer system 101 may act as a controller connected to an IVD device 107 of the analysis system 100 for performing an analysis of a biological sample. The IVD device 107 is adapted to perform one or more IVD tasks. An IVD task comprises a sequence of IVD actions. An IVD task may be for example a sample order task and/or a maintenance action task. A maintenance action task is shown in detail with reference to FIG. 6. Each IVD task of the one or more IVD tasks may be associated with a script 133 that is stored in the storage system 111. The script 133 comprises a list of instructions to guide a user to activate a respective list of IVD actions of the IVD task. The script 133 may be identified by a script ID. The list of IVD tasks and associated scripts ID are stored in table 135 in the memory system 105.

A simplified structure of the script 133 is shown in FIG. 1. The script 133 contains multiple fields and records or rows. For example, every record of the script 133 may be associated with a respective IVD action of the IVD task. Field 133.1 of the script 133 contains an incremented action ID of a given IVD action of the IVD task. Field 133.2 comprises names of user interface elements that are used to activate the given IVD action. Field 133.3 of the script 133 contains a text message indicative of the given IVD action. Field 133.4 contains an instruction to be executed for activating the given IVD action using the user interface elements named in field 133.2.

Memory system 105 is configured to store a plurality of applications that are executable on the processor 103. For example, the memory system 105 may comprise an operating system 137 as well as software applications 126. The operating system 137 comprises a window manager 139. The window manager 139 controls the placement and appearance of windows within a windowing system in a graphical user interface.

A first application 127 of the software applications 126 comprises instructions that, when executed, generate on the display device 113 a first user interface 121. For example, the first application 127 may be first started by a selection action of a user. After being started, the first application 127 may send a request to window manager 139 to start a window and provide the first user interface 121 to the running instance of the first application 127.

For sake of simplicity, the first user interface 121 is shown as comprising a set of 9 user interface elements A-I. However, persons of ordinary skill in the art having benefit of the present disclosure should appreciate that the first user interface 121 may contain higher or smaller number of user interface elements. Each user interface element in the set of user interface elements A-I is positioned in a defined region within the first user interface 121.

The user interface elements A-I may be positioned relative to the first user interface 121. The first user interface 121 contains the reference point. For example, the reference point may be either the top/left or bottom/right corner of the first user interface 121. The position of a user interface element may be described by a pair of X and Y values, each ranging from 0.0 to 1.0. These values represent, respectively, relative horizontal and vertical positions within the first user interface 121, with {X:0.0, Y:0.0} as the top left and {X:1.0, Y:1.0} as the bottom right. In addition, an element dimension defining the size property of the view of a user interface element may be specified using the width and height of the user interface element. As shown in FIG. 1, the position of the user interface element G may be described, for example, by the pair {$X_G$, $Y_G$}. Further, the view size of the user interface element G may be described by the height $H_G$ and the width $W_G$. In addition, the first user interface 121 may be positioned relative to the display device's top/left corner. However, persons of ordinary skill in the art having benefit of the present disclosure should appreciate that other positioning methods may alternatively be used.

Geometry data describing the positions, appearance and size of the user interface elements A-I as well as the first user interface 121 may be determined by the first application 127 and communicated to window manager 139. The following snapshot code shows an example code describing positions, appearance and size of the user interface elements A-I as well as the first user interface 121. The geometry data may be obtained, for example, by parsing the code and reading the position values as defined in the snapshot code.

```
<Window x:Class="MainWindow"
    Xmlns="http://schemas.microsoft.com/winfx/2006/xaml/presentation"
    xmlns:x="http://schemas.microsoft.com/winfx/2006/xaml"
    Title="Storyboard Updater" Height="738" Width="739" Name="frmMain">
    <Grid>
        <Grid.ColumnDefinitions>
            <ColumnDefinition Width="139*" />
            <ColumnDefinition Width="578*" />
        </Grid.ColumnDefinitions>
        <TabControl Margin="12,60,12,12" Name="TabControl1" Grid.ColumnSpan="2">
            <TabItem Header="Routine" Name="TabItem1">
                <Grid>
                    <Grid.ColumnDefinitions>
```

-continued

```
        <ColumnDefinition Width="104*" />
        <ColumnDefinition Width="579*" />
    </Grid.ColumnDefinitions>
    <ListBox Margin="10,37,331,95" Name="1stDocuments"
SelectionMode="Extended"
        <Label Content="Open all documents to be updated" FontSize="16" Height="39"
        <Button Content="Open selected documents" Height="42" HorizontalAlignment="
        <Button Content="Update Lists" HorizontalAlignment="Right" Margin="0,0,111,
        <Label Content="Status Label" Margin="183,0,43,54" Name="1b1Status" Height=
        <TextBox Margin="0,37,6,95" Name="txtPics" HorizontalAlignment="Right" Widt
        <Label Content="Documents" Height="31" HorizontalAlignment="Left" Margin="9
        <Label Content="Images" Height="31" HorizontalAlignment="Right" Margin"0,0"
        <Button Content="Start update" FontFamily="Segoe UI" Height="42" Horizontal
        <Button Content="Open Project" Height="42" HorizontalAlignment="Left" Margi
    </Grid>
</TabItem>
```

Alternatively, window manager 139 may be responsible for determining the appearance, size and screen position of the user interface elements A-I and the first user interface 121. In this case, the geometry data may be obtained, for example, from the window manager 139 using a process ID of the running instance of the first application 127. The process ID may be obtained for example using the name of the first application 127 as shown in the following screenshot of a terminal listing running processes on a Unix operating system. The first column lists the process IDs or running processes.

```
16087  ??  IW   0:00.04  bash /home/users/t/ta/tanders/src/net-snmp-
                         main/dist/ns
16200  ??  DW   0:00.00  grep -v ^*+ conftest.er1
16610  ??  IW   0:04.82  /bin/bash /home/users/t/ta/tanders/src/net-
                         snmp-V5-1-pa
16929  ??  I    0:00.16  sh Compile cvs/RELEASE wxGTK
17066  ??  I    0:00.00  sh Compile cvs/RELEASE wxGTK
17686  ??  IW   0:00.03  bash /home/users/t/ta/tanders/sro/net-snmp-
                         main/dist/ns
17774  ??  IW   0:06.28  /bin/bash /home/users/t/ta/tanders/srC/net-
                         snmp-V5-3-pa
18239  ??  I    0:00.00  sh Compile cvs/RELEASE wxGTK
19497  ??  IWs  0:00.12  sshd: tanders@notty
23894  ??  S    0:00.07  gmake
```

After being determined, the geometry data may be stored in the storage system 111.

The software applications 126 further comprise a second application 129. The second application 129 comprises instructions that, when executed, generate on the display device 113 a second user interface 123. For example, the second application 129 may be started after selecting a user interface element 125 of the first user interface 121. The user interface element 125 may be for example a help menu bar or a context menu bar, wherein the menu bar lists the one or more IVD tasks. The second user interface 123 may be used to guide the user of the system 100 to enter data to the first user interface 121 to perform an IVD task that is selected when selecting the user interface element 125.

The operation of the analysis system 100 will be described in detail with reference to FIG. 2-FIG. 5.

Figure 2:
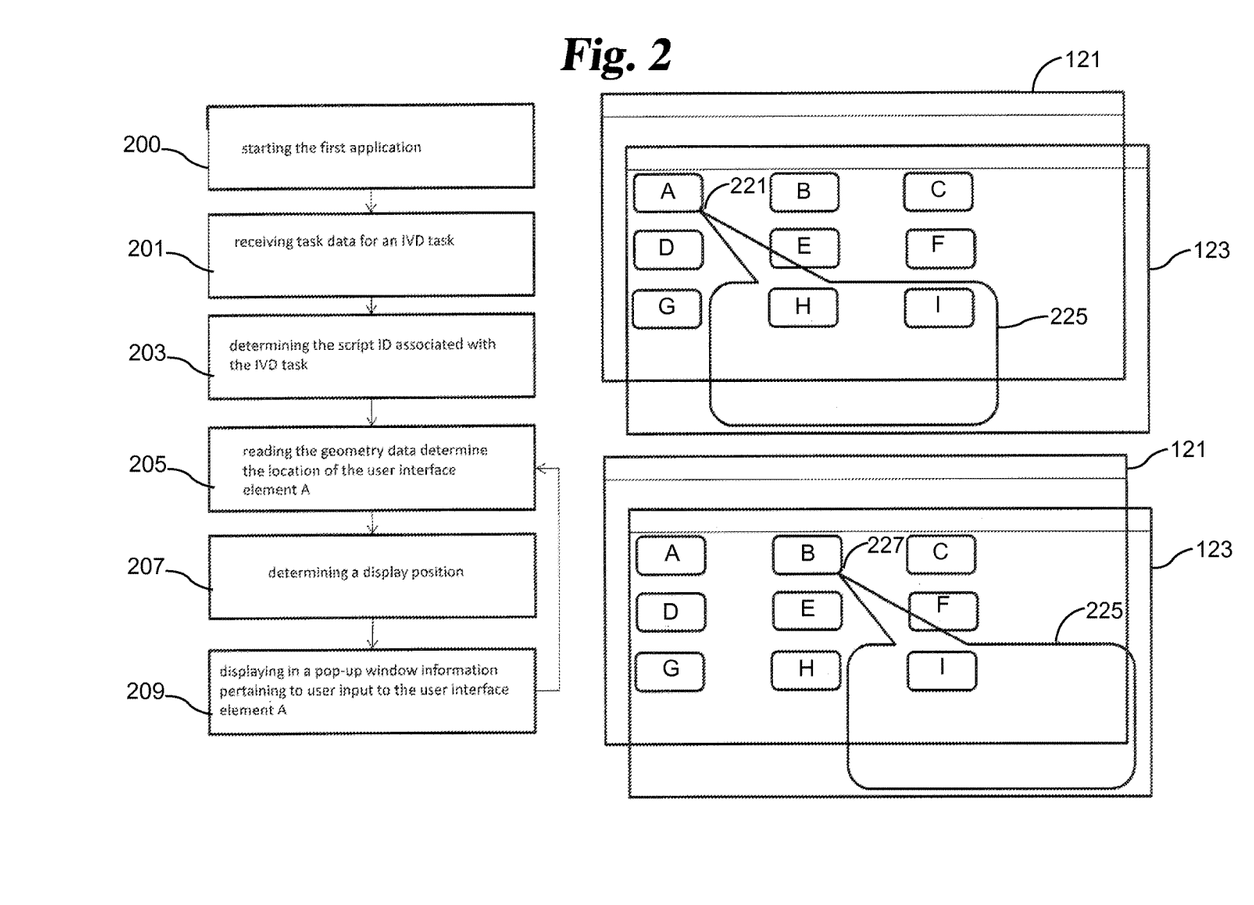
FIG. 2 is a flowchart of a method for guiding user input to a controller.

FIG. 2 is a flowchart of a method for guiding user input to a controller of the analysis system 100. The controller may be the computer system 101. In step 200, the first application 127 is started by a user of the analysis system 100, and the first user interface 121 is generated.

In step 201, the second application 129 may receive task data for an IVD task. The task data may be received upon initiation of the IVD task e.g. by the user. This initiation may be done, for example, by selecting a user interface element 125 of the first user interface 121 that is associated with the IVD task. The selection of the user interface element 125 also triggers the generation of the second user interface 123. The first and second user interfaces 121 and 123 may be displayed on the display device 113 such that the second user interface 123 is on top of the first user interface 121 and covers at least part of the first user interface 121.

In step 203, the second application 129 may read the table 135 to determine the script ID associated with the IVD task and load a script associated with the script ID initiation may be done, for example, by selecting a user interface element 125 of the first user interface 121 that is associated with the IVD task. The selection of the user interface element 125 also triggers the generation of the second user interface 123. The first and second user interfaces 121 and 123 may be displayed on the display device 113 such that the second user interface 123 is on top of the first user interface 121 and covers at least part of the first user interface 121.

In step 203, the second application 129 may read the table 135 to determine the script ID associated with the IVD task and load a script associated with the script ID from the storage system 111. Further, the second application may read the field 133.2 of the loaded script for determining a subset of user interface elements of the set of user interface elements A-I to be used to perform the IVD task. For simplicity of the description, the IVD task may comprise a sequence of three IVD actions and the subset of user elements may comprise the user interface elements A, F and G. For example, the user interface elements A, F and G may be associated with the first, second and third IVD action of the sequence of actions respectively. That is, the user may be sequentially guided to provide inputs into A, F and G in order to activate the first, second and third actions respectively.

Starting from the first user interface element A, the second application 129 may read in step 205, the geometry data e.g. the pair of $(X_A, Y_A)$ and $(H_A, W_A)$ values of the user interface element A stored in the storage system 111 to determine the location of the user interface element A within the first user interface 121.

In step 207, the second application 129 may determine based on the location of the user interface element A a corresponding display position 221 for displaying information in the second graphical user interface 123 using the location.

In step 209, the second application may display in a pop-up window 225, information pertaining to user input to the user interface element A that activates the first IVD action of the sequence of IVD actions of the IVD task. The pop-up window 225 may overlay at least a portion of the second user interface 123. The structure of the displayed information in the pop-up window 225 is described in details with reference to FIG. 5.

Upon activation of the first IVD action, the second application 129 may repeat steps 205-209 for each of the remaining user interface elements F and G. For example, in the second iteration for the user element F, the pop-up window may be positioned at the new defined display position 227.

After receiving user inputs to activate the three IVD actions, the IVD device 107 may be controlled to perform the IVD task using the received user inputs.

Figure 3:
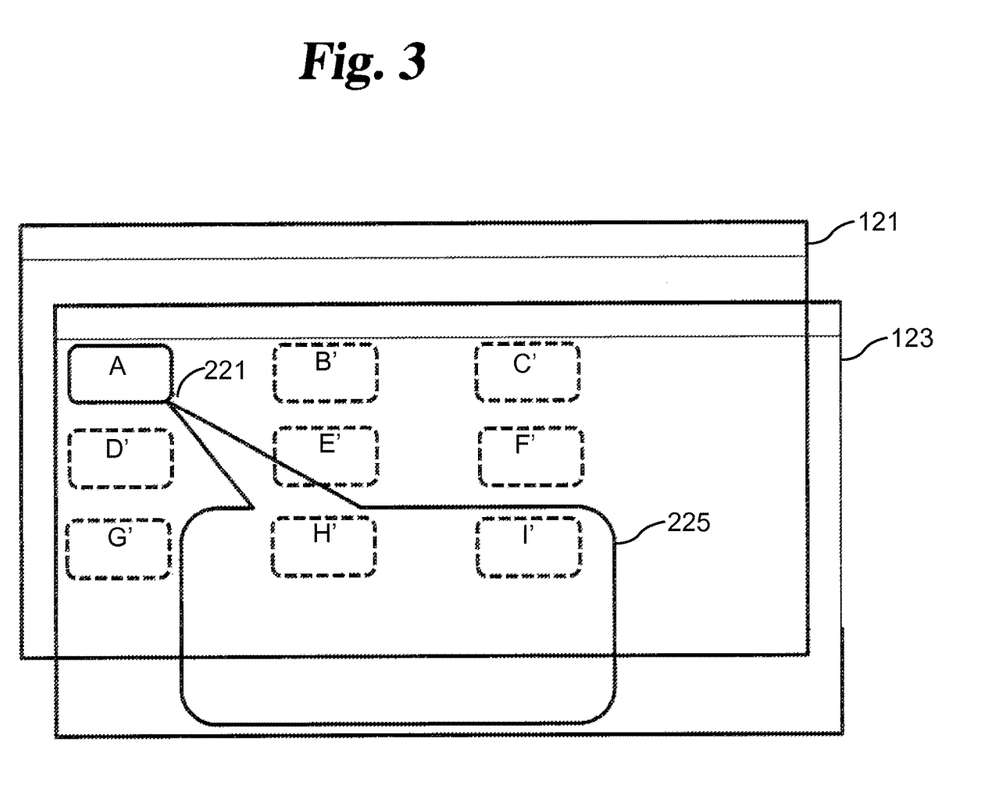
FIG. 3 illustrates a method for further defining step 207 of FIG. 2.

FIG. 3 illustrates a method for positioning the second and first user interfaces for further defining step 207 of FIG. 2. In this example, the second user interface 123 is positioned on top of the first user interface 121 such that it prevents access to the user interface elements B-I, and only allows access to the user interface element A. That is, user interface element A may be active in contrast to the user interface elements B-I and the user may only enter input data into the user interface element A that is in the background of the second user interface 123 (e.g. the operating system 137 may provide a function that may allow the user to enter data into a background user interface that is overlaid by another base station). The second user interface 123 may display a mask that is at least partially transparent or semitransparent, such that the user may continue viewing the user interface elements B-I in the first user interface 121 for which access is prevented. In an alternative example, the mask may hide the user interface elements B-I for which access is prevented. In another alternative example, the mask may hide the user interface elements B-E and H-I which are not used to perform the IVD task, and may be transparent for viewing the user interface elements F and G. This may prevent wrong user inputs to the user interface element A as the user may have an overview of all user interface elements A, F and G used for the IVD task.

Figure 4:
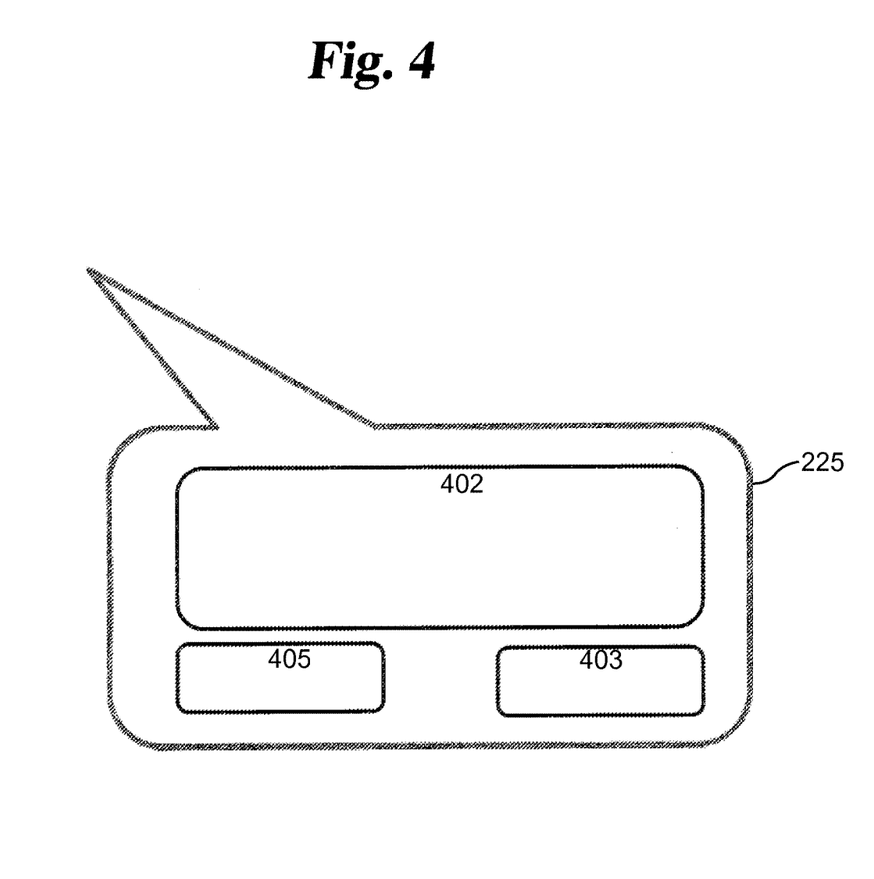
FIG. 4 shows an exemplary structure of a pop-up window.

FIG. 4 shows an exemplary structure of the pop-up window 225. The pop-up window 225 may include content that may guide the user to enter data into the first user interface 121 without having to navigate away from first and second user interface 121 and 123. The pop-up window 225 comprises a field 402 for displaying information pertaining to user input to the first user interface 121 for a previous IVD action or for a subsequent IVD action in the sequence of IVD actions of the IVD task.

The content of the field 402 may be obtained by reading the message in the field 133.3 of the script 133 and copying the read message to the field 402. The pop-up window 225 further comprises a continue icon 403 that is when selected a following or a previous action of the sequence of actions is to be performed. The continue icon 403 is displayed based on the information read by the second application 129 in the field 133.4 of the script 133 associated with the IVD task. The pop-up window may further comprise a cancel icon 405 for canceling an IVD action.

Figure 5:
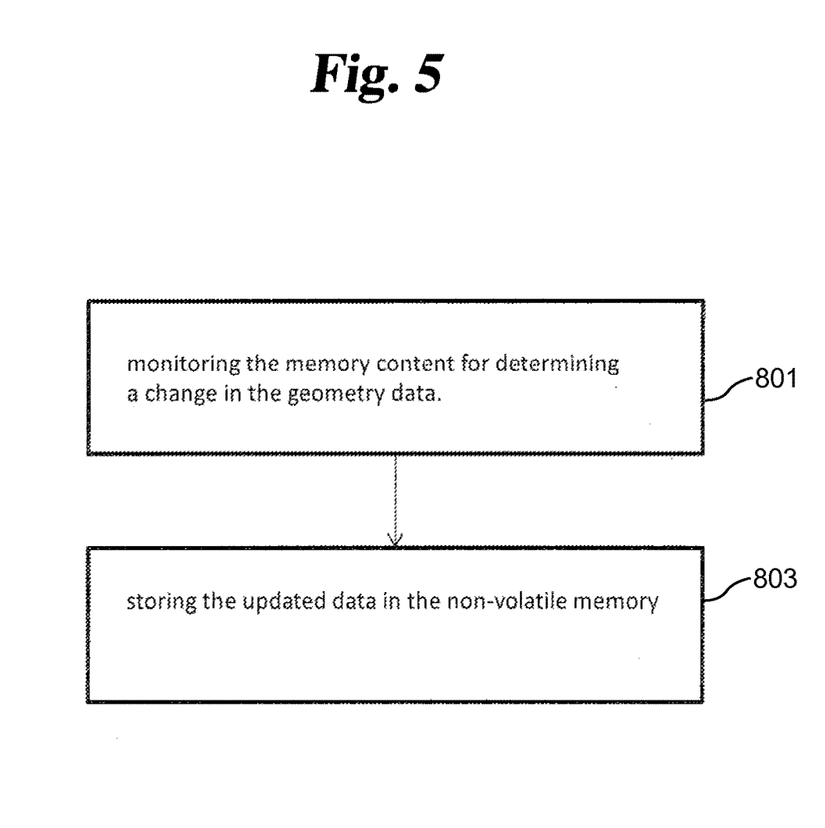
FIG. 5 shows a flowchart further defining step 205 of FIG. 2.

FIG. 5 shows a flowchart further defining step 205 of FIG. 2. In step 501 the second application 129 monitors the memory content for determining a change in the geometry data. For example, the change may be due to a resizing of the first user interface 121. The monitoring may be done on a periodic basis. In an alternative example, the second application 129 may repeatedly receive a status message regarding the geometry data. The update status message is indicative of the change in the geometry data. In step 503, the second application stores the updated data in the non-volatile memory 118 of the memory system 105, and moves the non-updated geometry into the volatile memory 117. This is because, the non-updated data may no longer required by the second application 129. The location is then determined in step 205 using the updated geometry data.

Figure 6:
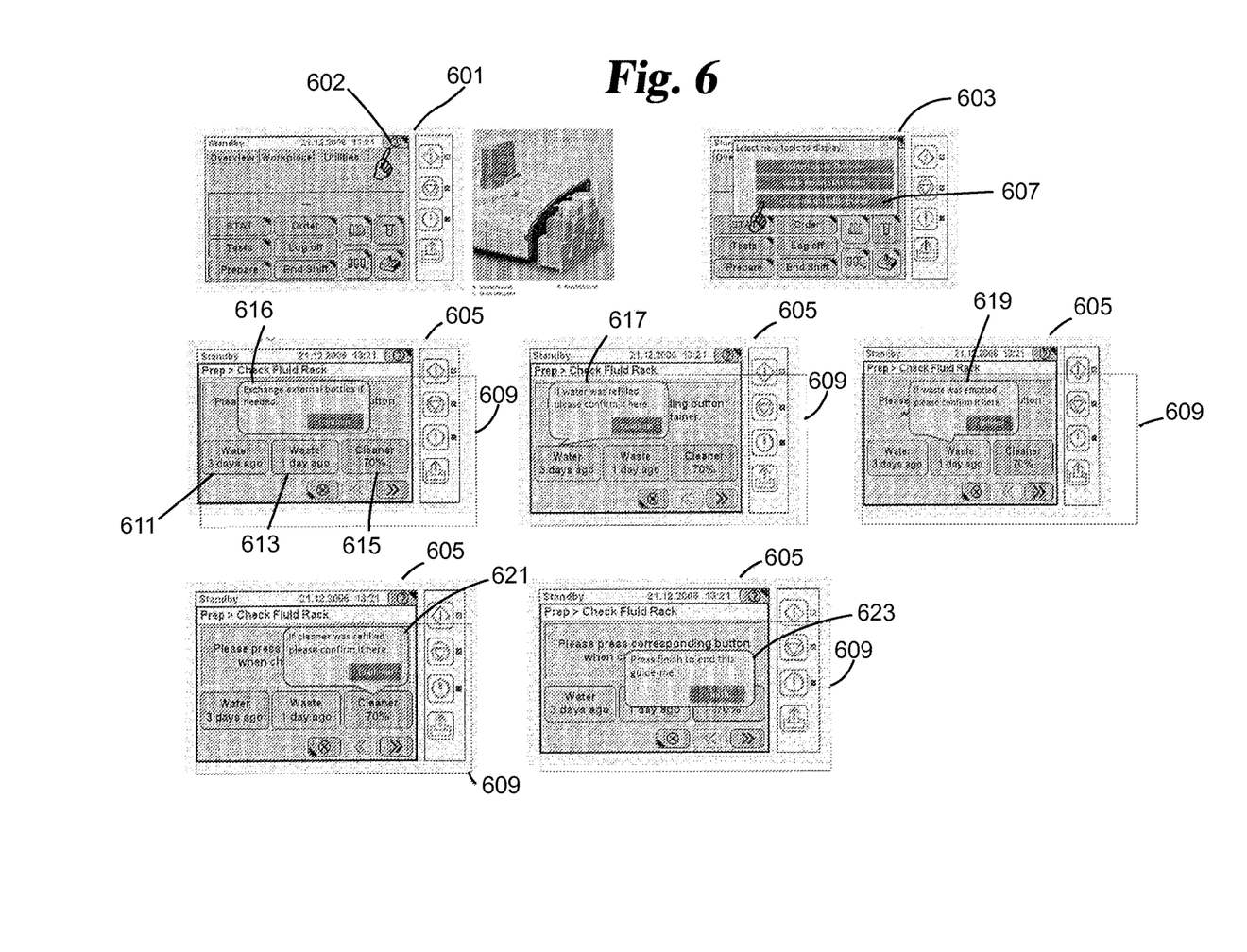
FIG. 6 shows analysis steps for checking external bottles of an analysis system.

FIG. 6 shows analysis steps for checking external reagent bottles of an analysis system measuring serum and urine samples. The external bottles comprise a water bottle, a cleaner bottle and a waste bottle. A user interface 601 generated by a software application such as the first application 127 is shown. The user interface 601 comprises a help menu bar element 602 that may be selected by a user of the analysis system to list the tasks that may be performed by the analysis system. The list of tasks is displayed on the user interface 605 after selecting the menu bar element 602. The user may select the user interface element 607 that is associated with the task of changing the bottle. A second user interface 609 is then displayed on top of the user interface 605. The user interface 605 shows the user interface elements 611, 613 and 615 that are used to perform the task. In the second user interface 609 the pop-up windows 616, 617, 619, 621 and 623 may be displayed in the second user interface 609 to guide the user to enter user input to perform the task. The pop-up windows 617, 619 and 621 are displayed in accordance with the user interface elements 611, 613 and 615 respectively.

LIST OF REFERENCE NUMERALS 100 analysis system
101 computer system
103 processor
105 memory system
107 IVD device
109 network adapter
111 storage system
113 display device
117 volatile memory
118 non-volatile memory
119 I/O user interface
121-123 graphical user interface
A-I, 125 user interface element
126 software applications
127-129 applications
133 script
133.1-4 fields
135 table
137 operating system
139 window manager
221, 227 display position
225, 616-623 pop-up window
402-405 fields
601, 603, 605, 609 user interface
602, 611-615 user interface element.

The invention claimed is:

1. An analysis system for processing biological samples comprising:
an in vitro diagnostic, IVD, device for performing an analysis of a biological sample, the IVD device being coupled to a computer system, the computer system comprising a display device; a processor; and memory configured to store a plurality of applications that are executable on the processor, wherein a first application of the plurality of applications comprises instructions that, when executed, generate on the display device a first graphical user interface, the first graphical user interface comprising a set of user interface elements (A-I), wherein each user interface element in the set of user interface elements (A-I) is positioned in a defined region within the first graphical user interface; the first application further comprising instructions that, when executed, control the IVD device to perform an IVD task; wherein the IVD task comprises a sequence of IVD actions; wherein an IVD action is performed in response to user activation of the IVD action, wherein the user activation of the IVD action is performed using a corresponding user interface element of the set of user interface elements (A-I); and wherein the memory further comprises geometry data describing a display position for each of the set of user interface elements (A-I) within the first graphical user interface;

wherein a second application comprises instructions that are executed independently of the first application, wherein the second application is configured to guide user input to the first graphical user interface for activating the IVD actions of the IVD task, the second application being further configured to: receive task data indicative of the sequence of IVD actions of the IVD task; select from the set of user interface elements (A-I) a subset of user interface elements that are used to perform the sequence of IVD actions of the IVD task; determine, using the geometry data, a location of each of the subset of user interface elements within the first graphical user interface; determine based on the location of each of the subset of the user interface elements in the first graphical user interface a corresponding display position for displaying information in a second graphical user interface; and display in the corresponding display position of the second graphical user interface, information pertaining to user action to at least one user interface element of the first graphical user interface that activates at least one particular IVD action of the sequence of IVD actions of the IVD task;

wherein the IVD device is configured to perform the IVD task in response to the user input to the first graphical user interface guided by the second application;

wherein the memory includes a common table used by both the first application and the second application for exchanging information between the first application and the second application;

wherein the information includes a script ID associated with the IVD task performed by the first application;

wherein the second application is configured to read the script ID from the common table and determine a subset of user interface elements based on the script ID;

wherein the memory includes a volatile memory space and a non-volatile memory space;

wherein the first application is configured to store the geometry data in the memory;

wherein the second application is configured to monitor the memory to determine a change in the geometry data;

wherein the second application is configured to determine updated geometry data and non-updated geometry data of the subset of the user interface elements within the first graphical user interface and change the second graphical user interface based on the updated geometry data; and wherein the second application is configured to store the updated geometry data in the non-volatile memory space and the non-updated geometry data in the volatile memory space.

2. The analysis system of claim 1, wherein the second application is further configured to receive user input to a second graphical user interface that causes the second application to display information pertaining to user input to the first graphical user interface for a previous IVD action or for a subsequent IVD action in the sequence of IVD actions of the IVD task, to cause the second application to display in the second graphical user interface additional or less information regarding user input to the first graphical user interface for the particular IVD action for which information is currently displayed in the second graphical user interface, and/or to call up or switch to a third application that a user can employ to determine an input to the user interface element for the particular IVD action for which information being currently displayed in the second graphical user interface.

3. The analysis system of claim 1, wherein the second application generates a mask in the second graphical user interface that masks at least part of the first graphical user interface of the display device and prevents access to at least one interface element in the first graphical user interface.

4. The analysis system of claim 3, wherein the mask generated by the second application in the second graphical user interface prevents access to all interface elements in the first graphical user interface except for at least one interface element in the first graphical user interface that corresponds to the particular IVD action for which the information is currently displayed in the second graphical user interface, thereby allowing a user to interact only with the interface element in the first graphical user interface that relates the particular IVD action to the information is currently displayed in the second graphical user interface.

5. The analysis system of claim 3, wherein the mask generated by the second application in the second graphical user interface is at least partially transparent or semitransparent, thereby permitting a user to continue viewing at least one of the interface elements in the first graphical user interface for which access is prevented.

6. The analysis system of claim 3, wherein the second application generates an indication and/or displays information in the second graphical user interface when a user attempts to interact with an interface element in the first graphical user interface for which access is prevented by the mask generated by the second application.

7. The analysis system of claim 1, wherein the memory further comprises an operating system, wherein the operating system comprises a window manager, wherein the window manager is providing the geometry data, wherein the determining of the location and the determining of the corresponding display position for displaying information in the second graphical user interface are performed using the geometry data obtained from the window manager.

8. The analysis system of claim 1, wherein the generation of the first graphical user interface further comprises generating a user interface element in the first graphical user interface that can be selected by a user to start execution of the second application.

9. The analysis system of claim 1, wherein the second application is executed automatically upon executing at least a part of the first application.

10. The analysis system of claim 1, wherein the computer system comprises a touch screen computer and wherein the display device is a touch sensitive display screen.

11. The analysis system of claim 1, wherein the second application is further configured to guide data input to a third graphical user interface for performing a second IVD task, wherein the third graphical user interface is generated by a third application of the plurality of applications stored in the memory.

12. The analysis system of claim 11, wherein the third graphical user interface is displayed in a separate user interface window or on a second display device.

13. The analysis system of claim 1, wherein the IVD task includes checking external reagent bottles for the IVD device.

14. The analysis system of claim 1, wherein the IVD task includes analyzing measurement values from the biological sample.

15. A method for operating an analysis system, the analysis system comprising a controller, an in vitro diagnostic, IVD, device for performing an analysis of a biological sample, the IVD device being coupled to the controller, the controller comprising a display device; a processor; and memory configured to store a plurality of applications that are executable on the processor, wherein a first application of the plurality of applications comprises instructions that, when executed, generate on the display device a first graphical user interface, the first graphical user interface comprising a set of user interface elements (A-I), wherein each user interface element in the set of user interface elements (A-I) is positioned in a defined region within the first graphical user interface; the first application further comprising instructions that, when executed, control the IVD device to perform an IVD task; wherein the IVD task comprises a sequence of IVD actions; wherein an IVD action is performed in response to user activation of the IVD action, wherein the user activation of the IVD action is performed using a corresponding user interface element of the set of user interface elements (A-I), wherein the plurality of applications include a second application, wherein the memory includes a table used by both the first application and the second application for exchanging information between the first application and the second application; and, wherein the memory further comprises geometry data describing a display position for each of the set of user interface elements (A-I), wherein the memory includes a volatile memory space and a non-volatile memory space; the method comprising the following steps for guiding a user's input into the controller:

receiving task data for an IVD task in the form of a script ID stored in the table that is indicative of the sequence of IVD actions of the IVD task, wherein said receiving the task data includes reading with the second application the script ID from the table;

selecting with the second application from the set of user interface elements (A-I) a subset of user interface elements that are used to perform the sequence of IVD actions of the IVD task based on the script ID;

determining, using the geometry data, a location of each of the subset of user interface elements within the first graphical user interface;

storing the geometry data in the memory with the first application;

monitoring the memory with the second application to determine a change in the geometry data;

determining based on the location of each of the user interface elements of the subset of the user interface elements a corresponding display position for displaying information in a second graphical user interface using the location with the second application;

determining with the second application updated geometry data and non-updated geometry data of the subset of the user interface elements within the first graphical user interface and change the second graphical user interface based on the updated geometry data;

storing the updated geometry data in the non-volatile memory space and the non-updated geometry data in the volatile memory space;

displaying in the corresponding display position of the second graphical user interface, information pertaining to user action to at least one user interface element of the first graphical user interface that activates at least one particular IVD action of the sequence of IVD actions of the IVD task;

receiving an input from the user for the at least one user interface element in response to said displaying; and performing the at least one particular IVD action in response to said receiving the input.

16. A computer program product comprising computer executable instructions to perform the method steps of the method of the claim 15.

17. The method of claim 15, further comprising preventing interaction with the user interface elements not within the subset of user interface elements from said selecting to prevent accidental performance of IVD actions not part of the IVD task.

18. The method of claim 17, wherein said preventing interaction includes masking the user interface elements not within the subset of user interface elements from said selecting.

19. The method of claim 15, wherein said performing further includes performing the IVD task with the IVD device.

20. The method of claim 19, wherein the IVD task includes analyzing measurement values from the biological sample.

* * * * *